(12) United States Patent
Rubatino et al.

(10) Patent No.: US 8,793,931 B2
(45) Date of Patent: Aug. 5, 2014

(54) PICK-UP AND DELIVERY SYSTEM AND ASSOCIATED METHODS

(75) Inventors: Fredrick T. Rubatino, Tacoma, WA (US); Michael W. Teodoro, Milton, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 424 days.

(21) Appl. No.: 13/156,096

(22) Filed: Jun. 8, 2011

(65) Prior Publication Data

US 2012/0003074 A1     Jan. 5, 2012

Related U.S. Application Data

(60) Provisional application No. 61/359,917, filed on Jun. 30, 2010.

(51) Int. Cl.
    *A01C 1/06*      (2006.01)

(52) U.S. Cl.
    USPC ........................................ 47/57.6; 47/58.1 SE (58) Field of Classification Search
    USPC ................................. 47/57.6, 1.01 R, 58.1 SE
    See application file for complete search history.

(56) References Cited

U.S. PATENT DOCUMENTS

| | | | |
|---|---|---|---|
| 4,995,662 A | | 2/1991 | Hawkswell |
| 5,456,510 A | * | 10/1995 | Coots et al. .................. 294/183 |
| 5,467,525 A | | 11/1995 | Pine et al. |
| 5,701,699 A | | 12/1997 | Carlson et al. |
| 5,745,241 A | * | 4/1998 | Hashimoto .................. 356/635 |
| 6,684,564 B1 | * | 2/2004 | Hirahara ........................ 47/57.6 |
| 6,931,787 B2 | | 8/2005 | Hirahara |
| 7,207,139 B2 | * | 4/2007 | McKinnis et al. ............. 47/57.6 |
| 7,603,807 B2 | * | 10/2009 | McKinnis et al. ......... 47/58.1 R |
| 2005/0108931 A1 | * | 5/2005 | McKinnis et al. ................. 47/10 |
| 2005/0114918 A1 | * | 5/2005 | Hirahara et al. .............. 800/278 |
| 2007/0170736 A1 | * | 7/2007 | McKinnis et al. ........... 294/64.1 |

* cited by examiner

*Primary Examiner* — Kristen C Hayes (74) *Attorney, Agent, or Firm* — Baker Hostetler LLP (57) ABSTRACT

The present disclosure relates to a pick-up and delivery system including a pick-up assembly and a delivery assembly. The pick-up assembly includes a robotic arm, a pick-up device rotatably mounted on the robotic arm, and a first vacuum pressure supply port operably connected to the pick-up device. The delivery assembly includes an insertion device and a second vacuum pressure supply port. The insertion device may include an insertion member and a release assistance rod arranged inside the insertion member. The release assistance rod is moveable between an extended position and a retracted position. When the release assistance rod is in the extended position, a proximal end extends beyond an end of the insertion member. Further aspects are directed towards methods for grasping and releasing an object with a pick-up and delivery system.

14 Claims, 12 Drawing Sheets

PICK-UP AND DELIVERY SYSTEM AND ASSOCIATED METHODS

CROSS-REFERENCE TO RELATED APPLICATIONS

This application is entitled to and claims the benefit of priority under 35 U.S.C. §119 from U.S. Provisional Patent Application Ser. No. 61/359,917 filed Jun. 30, 2010, and titled "Pick-up and Delivery System and Associated Methods," the contents of which are incorporated herein by reference.

This application relates to U.S. patent application Ser. No. 13/156,125, filed on the same day as the present patent application, and titled "Pick-up and Delivery System and Associated Methods" the contents of which are incorporated herein by reference.

TECHNICAL FIELD

The present disclosure is directed generally to material handling systems, and particularly to pick-up and delivery systems for use with plant embryos.

BACKGROUND

Modern agriculture, including silviculture, often requires planting of large numbers of substantially identical plants that are genetically tailored to grow optimally in a particular locale or to possess certain other desirable traits. Production of new plants by sexual reproduction can be slow and is often subject to genetic events resulting in variable traits in its progeny. As a result, asexual propagation has been shown to yield large numbers of genetically identical embryos for some species. Such embryos are typically further cultured under laboratory conditions until they mature into an autotrophic "seedling" state characterized by an ability to produce their own food via photosynthesis, to resist desiccation, to produce roots able to penetrate soil, and to fend off soil microorganisms.

Researchers have experimented in asexual propagation with the production of artificial seeds known as "manufactured seeds." Manufactured seeds typically include the following components: a seed shell, a synthetic gametophyte, and a plant embryo. A manufactured seed that does not contain a plant embryo is known in the industry as a "seed blank." The seed blank is typically a cylindrical capsule made from biodegradable plastic having an open end and a closed end. Manufactured seeds are produced by placing the synthetic gametophyte within the seed shell such that it substantially fills the interior of the seed shell. A longitudinally extending hard porous insert, known in the industry as a "cotyledon restraint," may be centrally located within the synthetic gametophyte. The cotyledon restraint includes a centrally located cavity extending partially through its length and is sized to receive the plant embryo. The plant embryo is approximately 4 to 7 millimeters in length and roughly 0.5 millimeters in diameter. The shape of the plant embryo is somewhat cylindrical, but is also irregular in cross-section and varies in diameter along its length. The plant embryo contains both a radicle (or root) end and a cotyledon end. The plant embryo is deposited into cavity of the cotyledon restraint oriented so that the cotyledon end is inserted first. Subsequently, the plant embryo is typically sealed within the seed shell using at least one end seal.

Numerous types of plant embryo delivery systems have been used to transfer the plant embryo through the manufactured seed production line. Examples of such systems include U.S. Pat. No. 6,684,564, U.S. Pat. No. 7,207,139, and U.S. Pat. No. 7,603,807, all of which are hereby incorporated by reference. Although known systems have been effective in transporting plant embryos, problems are often encountered. For example, in some applications, embryos are hydrated to prevent damage from desiccation. These moist and sticky embryos often remain attached to plant embryo delivery systems and may be damaged during removal attempts. Even if the embryo is not damaged, sticking can also cause improper orientation or placement in the seed shell. Either scenario results in the possibility of wasting viable embryos, which is costly in commercial applications.

Thus, there is a need in the industry to develop new systems and methods for plant embryo pick-up and delivery. Ideally such systems will be suitable for transferring a viable embryo through a manufactured seed production line with minimized sticking to the components and/or damage to the embryo.

SUMMARY

The following summary is provided for the benefit of the reader only and is not intended to limit in any way the invention as set forth by the claims. The present disclosure is directed generally towards material handling systems, and particularly to pick-up and delivery systems for use with plant embryos.

In some embodiments, the present disclosure relates to a pick-up and delivery system including a pick-up assembly and a delivery assembly. The pick-up assembly includes a robotic arm, a pick-up device rotatably mounted on the robotic arm, and a first vacuum pressure supply port operably connected to the pick-up device. The delivery assembly includes an insertion device and a second vacuum pressure supply port. The insertion device may include an insertion member and a release assistance rod arranged inside the insertion member. The release assistance rod is moveable between an extended position and a retracted position. When the release assistance rod is in the extended position, it extends beyond the proximal end of the insertion member.

Further aspects are directed towards methods for grasping and releasing an object with the pick-up and delivery system. In some embodiments, such methods include the steps of moving the pick-up device to a first location to grasp the object and supplying a first vacuum pressure to the tip opening of the pick-up device. The pick-up device and the object may then be moved to a second location. The object may be transferred from the pick-up device to the insertion member by supplying a second vacuum pressure to the insertion member and removing the first vacuum pressure while the release assistance rod is in the retracted position. The insertion member and the object may then be moved to the second position so that the object is located above a receptacle. The object may be inserted into the receptacle by removing the second vacuum pressure and moving the release assistance rod to the extended position.

BRIEF DESCRIPTION OF THE DRAWINGS

The present disclosure is better understood by reading the following description of non-limitative embodiments with reference to the attached drawings wherein like parts of each of the figures are identified by the same reference characters, and are briefly described as follows.

DETAILED DESCRIPTION

The present disclosure describes, generally, material handling systems, and, particularly, pick-up and delivery systems for use with plant embryos. Specifically the disclosure is directed to a pick-up and delivery system that grasps small objects such as those having dimensions of about 0.2 to about 10 millimeters in width and about 2 to about 20 millimeters in length. While the present disclosure describes examples used for handling plant embryos, it will be appreciated that the scope of the disclosure includes handling other objects having similar dimensions.

Certain specific details are set forth in the following description and FIGS. 1-12 to provide a thorough understanding of various embodiments of the disclosure. Well-known structures, systems, and methods often associated with such systems have not been shown or described in details to avoid unnecessarily obscuring the description of various embodiments of the disclosure. In addition, those of ordinary skill in the relevant art will understand that additional embodiments of the disclosure may be practiced without several of the details described below.

In this disclosure, the term "object" is used to describe any object having dimensions suitable for pick-up and delivery using systems according to the disclosure (e.g., plant embryos, plant tissue, any sort of seed) The term "plant embryo" is used to describe part of a seed consisting of precursor tissues for the leaves, stem, and root, as well as one or more cotyledons. The disclosure is not intended to be limited to any particular type of seed. For example, embodiments according to the disclosure are suitable for use with plant embryos related to agricultural seeds, seeds for producing trees, or any other type of seed.

Figure 1:
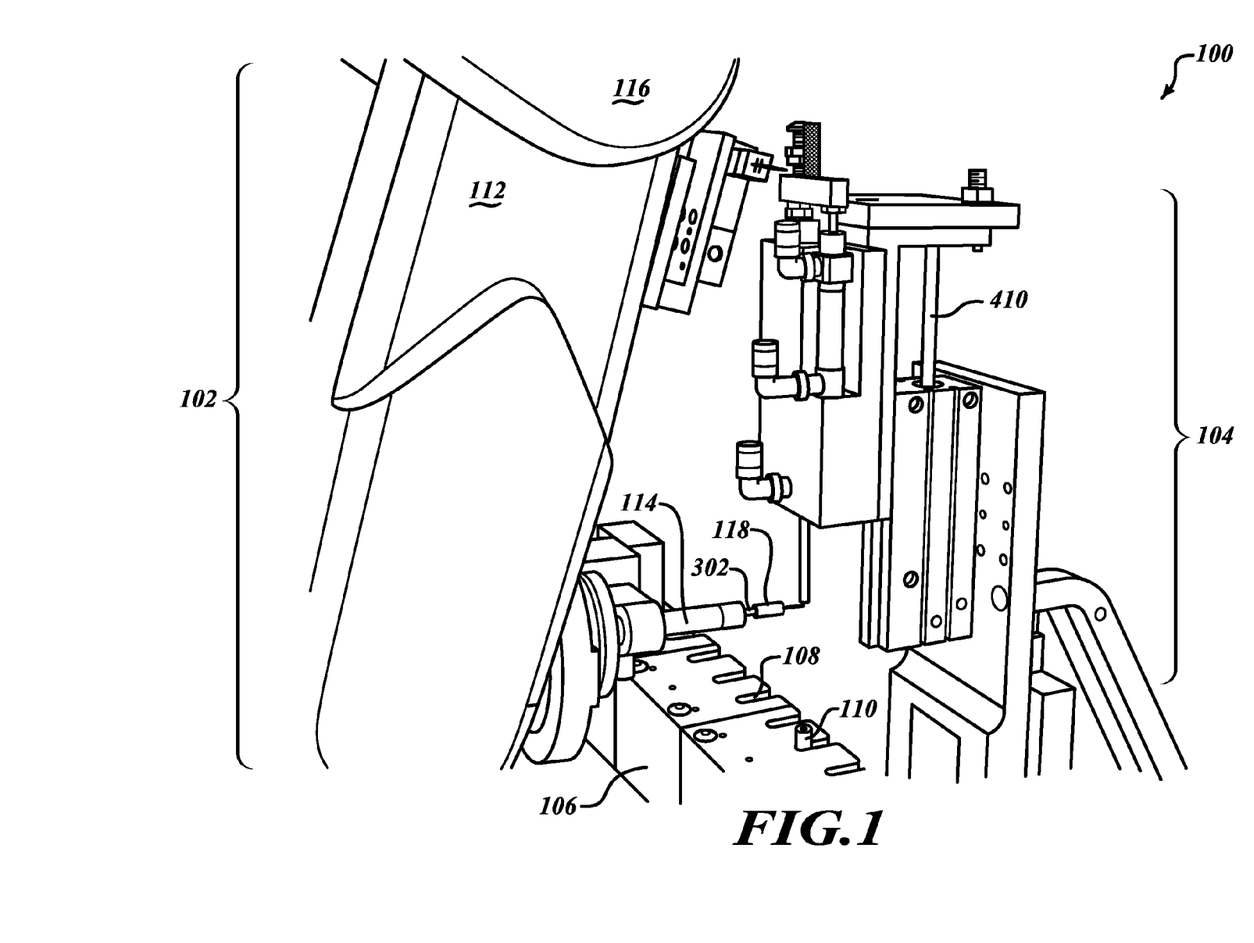
FIG. 1 is a schematic three-dimensional view of a pick-up and delivery system according to embodiments of the disclosure during embryo handoff.

FIG. 1 is a schematic three-dimensional view of a pick-up and delivery system 100 according to embodiments of the disclosure. The pick-up and delivery system 100 may include a pick-up assembly 102 and a delivery assembly 104. In some embodiments, the pick-up assembly 102 and the delivery assembly 104 are arranged on a storage assembly 106 as part of a production line. The storage assembly 106 may include one or more cavities 108, each of the one or more cavities 108 being configured to hold a receptacle 110. Each receptacle 110 is configured to hold one or more objects. The objects may have a diameter between about 0.2 to about 10.0 millimeters and a length between about 2.0 to about 20 millimeters.

Figure 2:
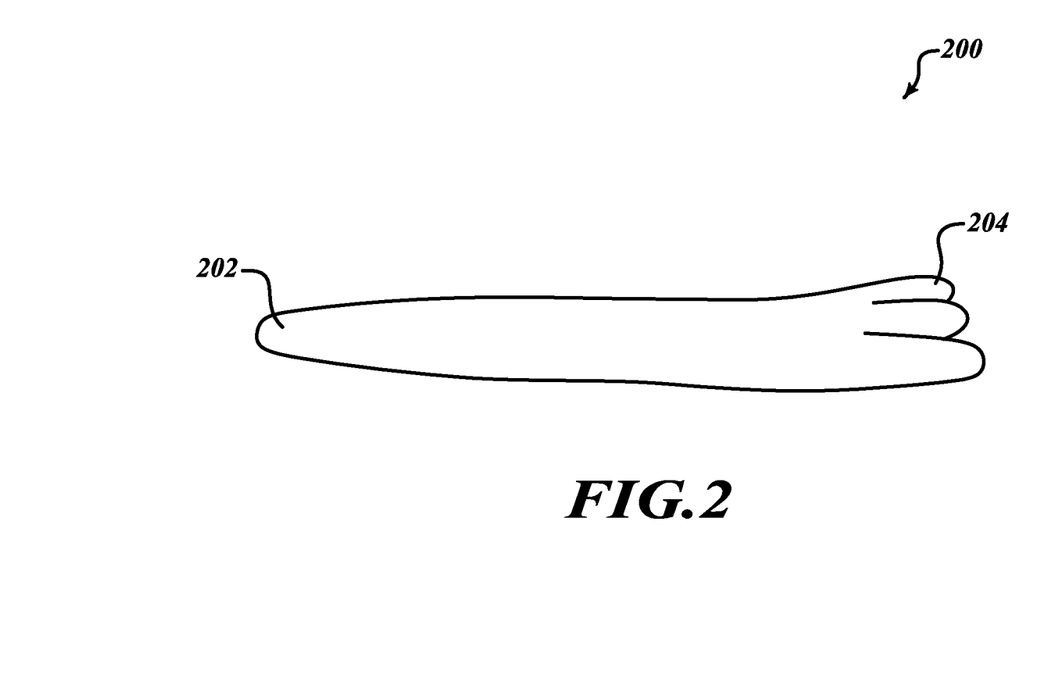
FIG. 2 is a side view of a plant embryo suitable for use with embodiments according to the disclosure.

In the Figures, the object is a plant embryo in a manufactured seed production line. Referring to FIG. 2, a plant embryo 200 is shown having a radicle (or root) end 202 and a cotyledon end 204. The root (or radicle) end 202 generally has the weakest cells, making it prone to damage. Referring back to FIG. 1, the one or more receptacles 110 may be seed shells having cotyledon restraint cavities. A person of ordinary skill in the art will appreciate that although the examples describe systems and methods for handling plant embryos, embodiments according to the disclosure may be used with other types of objects in other types of production lines. Further, while embodiments of the Figures show examples in which a single object is inserted into a receptacle, embodiments of the disclosure are intended to include systems for placing more than one object in a single receptacle.

Referring again to FIG. 1, the pick-up assembly 102 may include a robotic arm 112, a pick-up device 114, and a first vacuum supply port (not visible in FIG. 1). The robotic arm may have one or more hinge points 116 enabling it to translate and rotate in various directions with respect to the delivery assembly 104 and the storage assembly 106. The pick-up device 114 may be rotatably mounted on the robotic arm 112, allowing it to rotate 360 degrees.

Figure 3:
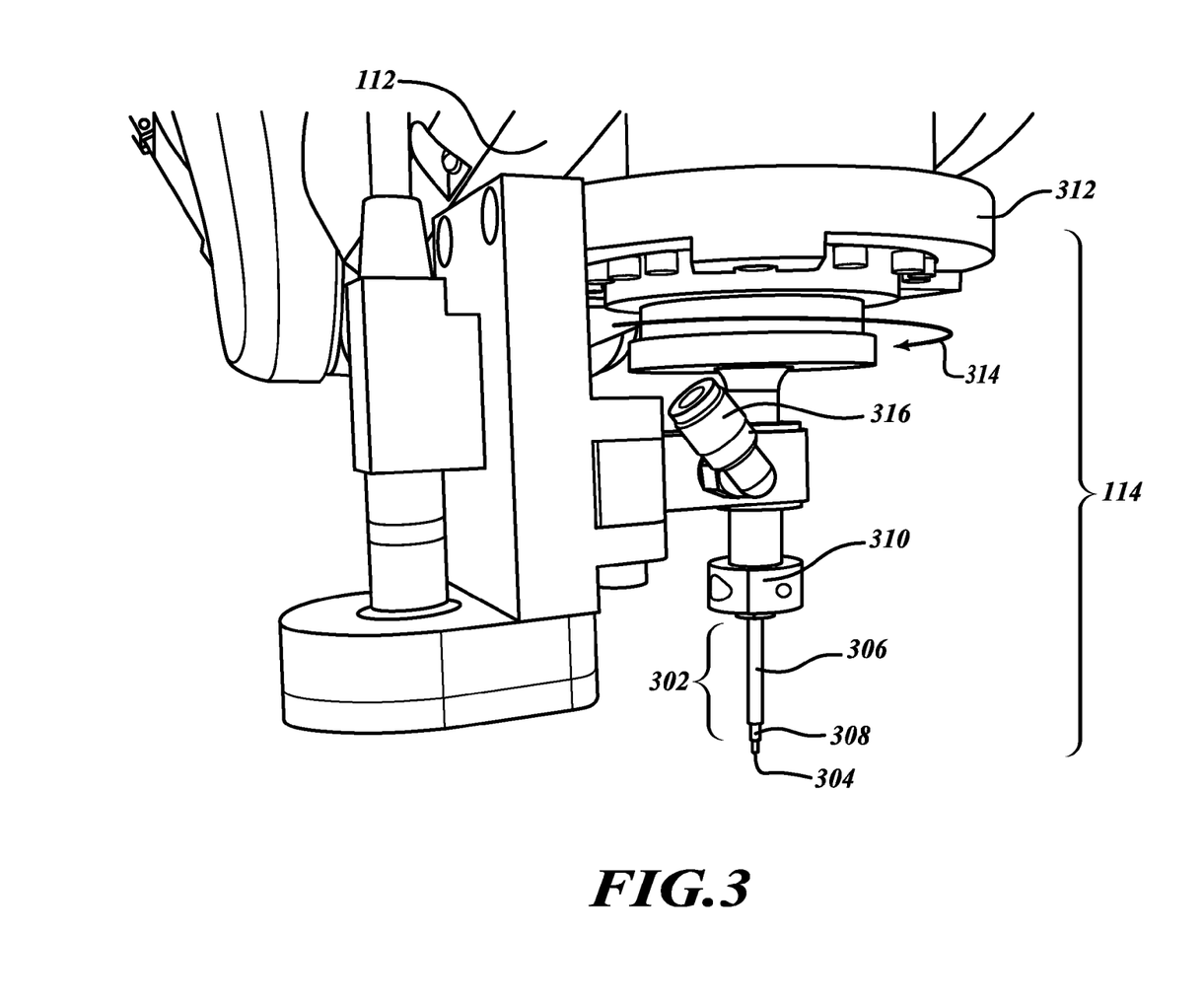
FIG. 3 is a schematic three-dimensional view of a pick-up device according to embodiments of the disclosure.
Figure 4:
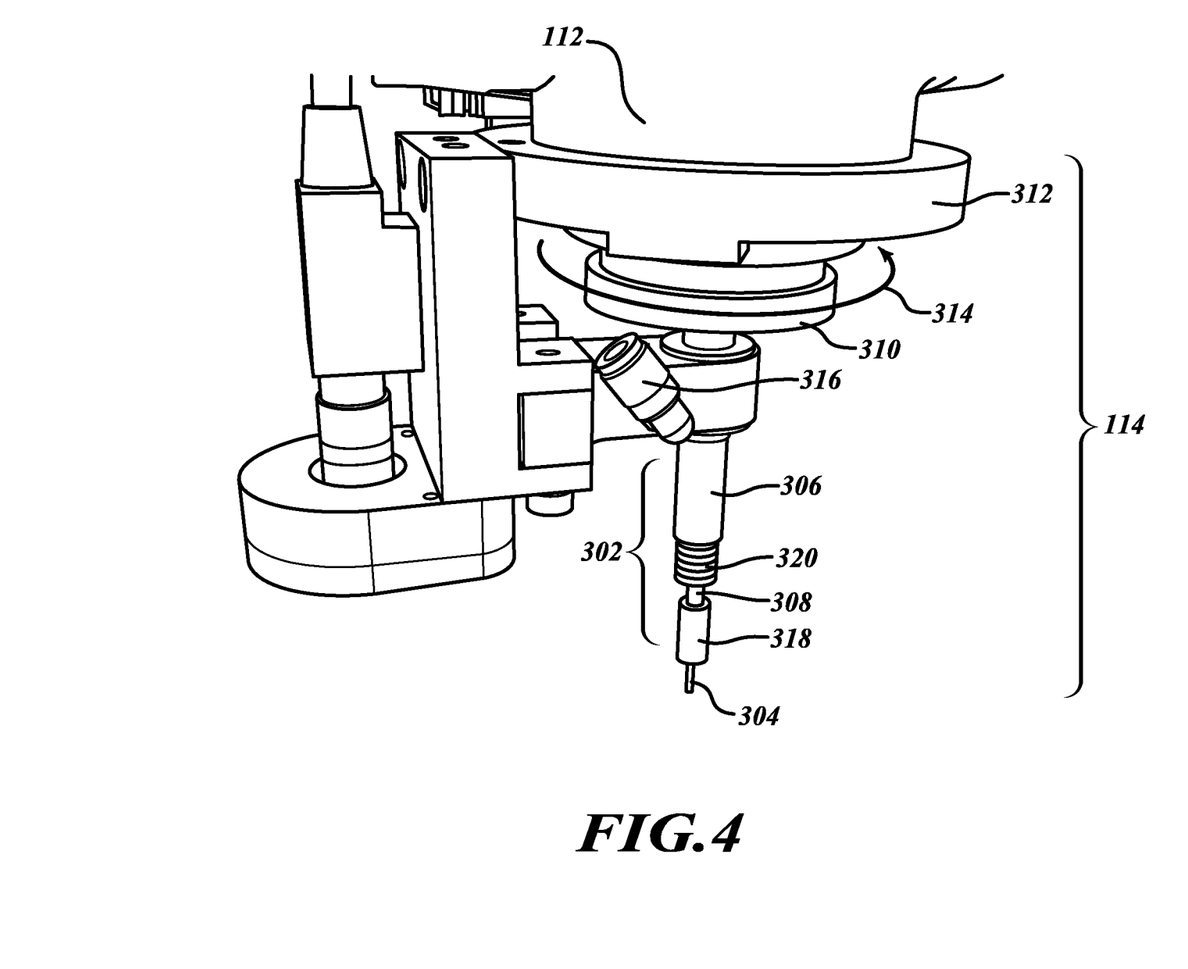
FIG. 4 is a schematic three-dimensional view of another pick-up device according to embodiments of the disclosure.

Components of embodiments of the pick-up assembly 102 will now be described in further detail. Referring to FIGS. 3 and 4, a schematic three-dimensional view of the pick-up device 114 according to embodiments of the disclosure is depicted. In FIGS. 3 and 4, the pick-up device 114 includes a tube member 302 and a tip opening 304. In some embodiments, the tube member 302 may include a first section 306 having a first diameter and a second section 308 having a second diameter. In some embodiments, the tube member 302 may be several concentric tubes of varying diameters. The tip opening 304 may be sized so that it is capable of picking up objects having dimensions of about 0.2 to about 10 millimeters in width and about 2 to about 20 millimeters in length. Embodiments of the disclosure include tip opening 304 which may pick up objects having varying sizes within this specified range. Components of the pick-up device 114 may be made from metal, Teflon, or other suitable materials known to a person of ordinary skill in the art.

The pick-up device 114 may be rotatably mounted on the robotic arm 112 using a first collar 310 and a second collar 312. Accordingly, the pick-up device 114 may rotate or spin as shown by arrow 314. A person of ordinary skill in the art will appreciate that mounting systems other than those explicitly shown in the Figures may be used provided such systems enable rotation and translation of the pick-up device 114.

Embodiments of the disclosure may be effective to balance the varied needs associated with material handling systems used for objects having the specified dimensions. On one hand, there are many reasons to minimize the tip opening 304 surface area contacting the object so that the object does not stick to the pick-up device 114. At the same time, if the tip opening 304 is too small, the object may be damaged during pick-up. Further, if the tube member 302 is too small, it may become unstable and wobble while it is being rotated and translated. Accordingly, the tube member 302 with sections having varied diameters (e.g., the first section 306 and the second section 308) may be provide stability during rotation and translation while the smaller tip opening 304 enables the pick-up device 114 to grasp and release varying sizes of objects without damage or sticking.

In FIGS. 3 and 4, a first vacuum supply port 316 is shown connected to the pick-up device 114. The first vacuum pressure supply port 316 is also connected to a vacuum pressure source (not shown). Accordingly, the first vacuum pressure supply port 316 may be configured to supply vacuum pressure to the tip opening 304 of the pick-up device 114.

In some manufactured seed production lines, machine vision systems are used for selection of embryos. Accordingly, in some embodiments, portions of the pick-up device 114 or the entire pick-up device 114 may be coated with a substance for reducing reflectivity. Referring back to FIG. 4, an exemplary coating 318 is shown on the pick-up device 114. Coatings 318 suitable for use with embodiments according to the disclosure include rubber, plastic, or any non-glossy material having shading that is in contrast to the color of the object. For example, if the object is light, the coating 318 should be dark and vice versa. In some embodiments such as the embodiment shown in FIG. 4, O-rings 320 may be surround portions of the tube member 320. Alternatively if the pick-up device 114 is constructed from metal, a portion of it may be sandblasted to reduce reflectivity.

Figure 5:
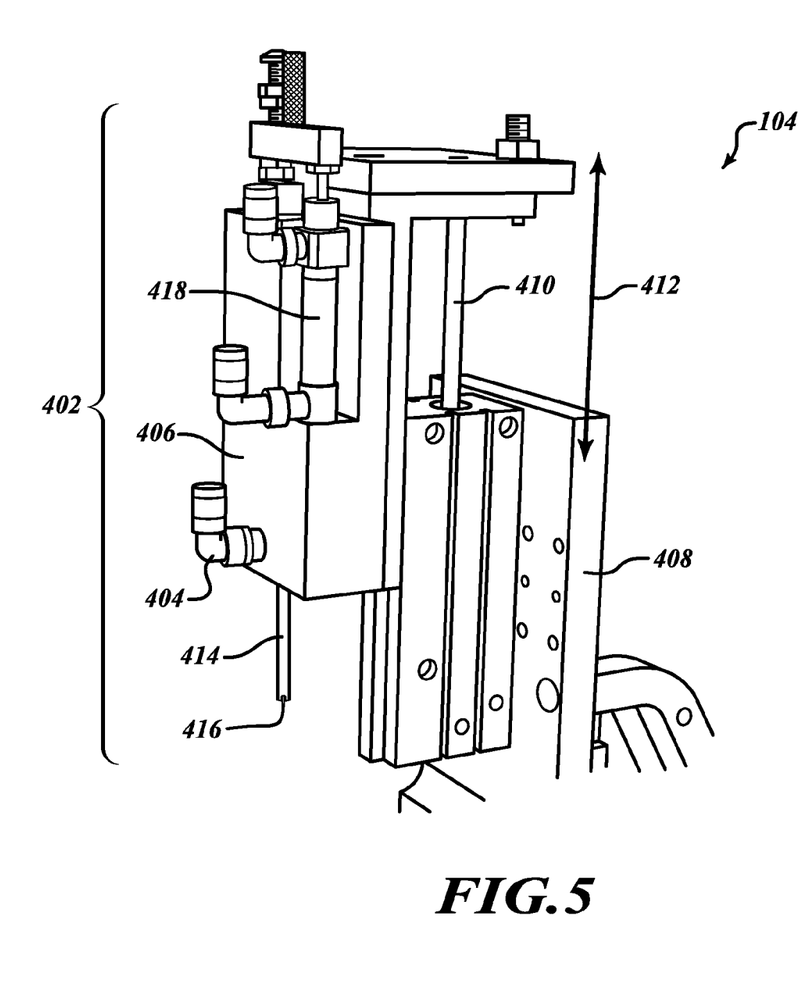
FIG. 5 is a schematic three-dimensional view of a delivery assembly in a first position according to embodiments of the disclosure.

Components of embodiments of the delivery assembly 104 will now be described in further detail. Referring to FIG. 5, a schematic three-dimensional view of the delivery assembly 104 according to embodiments of the disclosure is depicted. In FIG. 5, the delivery assembly 104 includes an insertion device 402 and a second vacuum pressure supply port 404. In some embodiments, the insertion device 402 includes a housing 406 mounted on a frame 408. The frame 408 may be located in a plane that is substantially perpendicular to the storage assembly 106 (not visible in FIG. 5). An actuation mechanism 410 (e.g., a piston) enables the insertion device 402 to be moved up and down (as indicated by arrow 412) between a first position (shown in FIGS. 1 and 5) and a second position (shown in FIG. 10) with respect to the storage assembly 106. The first position may be a raised position and the second position may be a lowered position. Alternatively, the first and second positions may be horizontal, skewed, or arranged in any other configuration known to a person or ordinary skill in the art. The actuation mechanism 410 may be a hydraulic actuation system, an electric actuation system, or any other actuation system known to a person of ordinary skill in the art. In FIG. 5, the insertion device 402 is shown in the first position. In some embodiments, the insertion device 402 is also moveable to a number of intermediate positions between the first position and the second position.

Figure 6:
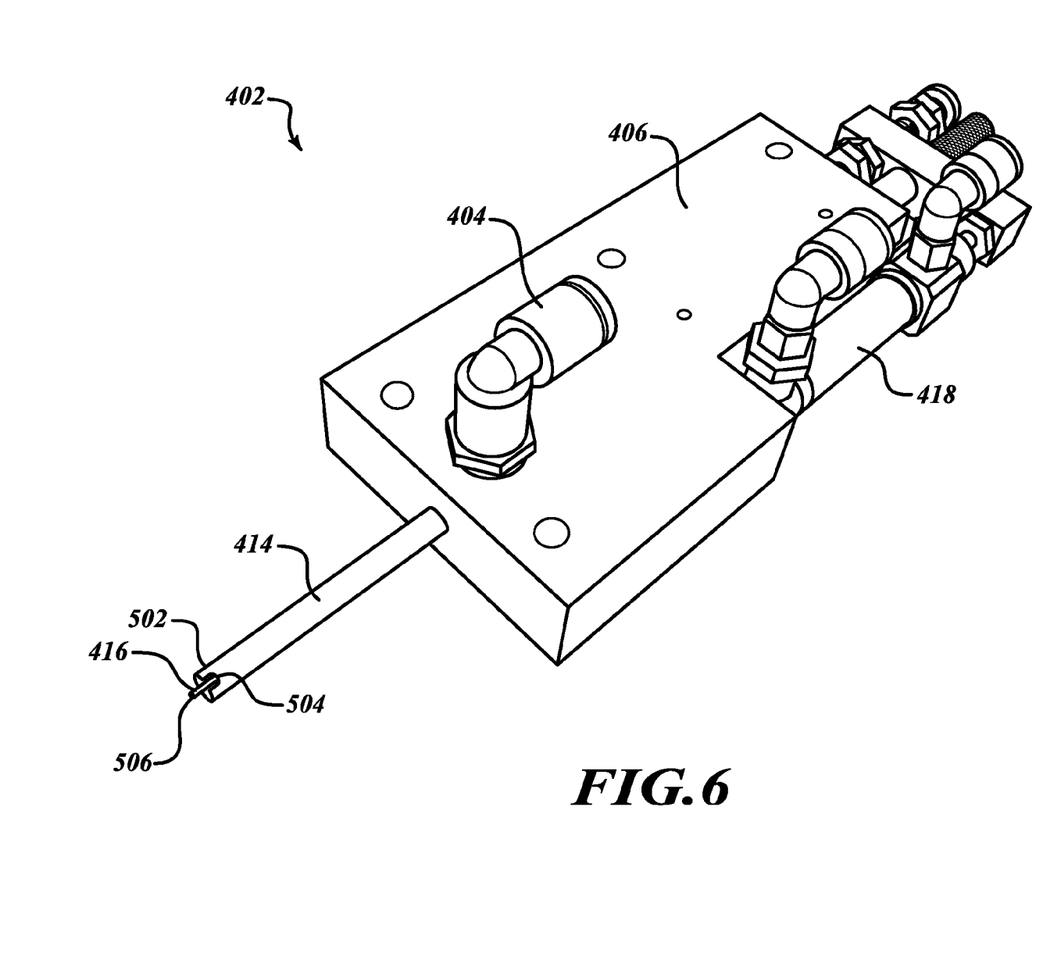
FIG. 6 is a schematic three-dimensional view of an insertion member and a release assistance rod in an extended position according to embodiments of the disclosure.
Figure 7:
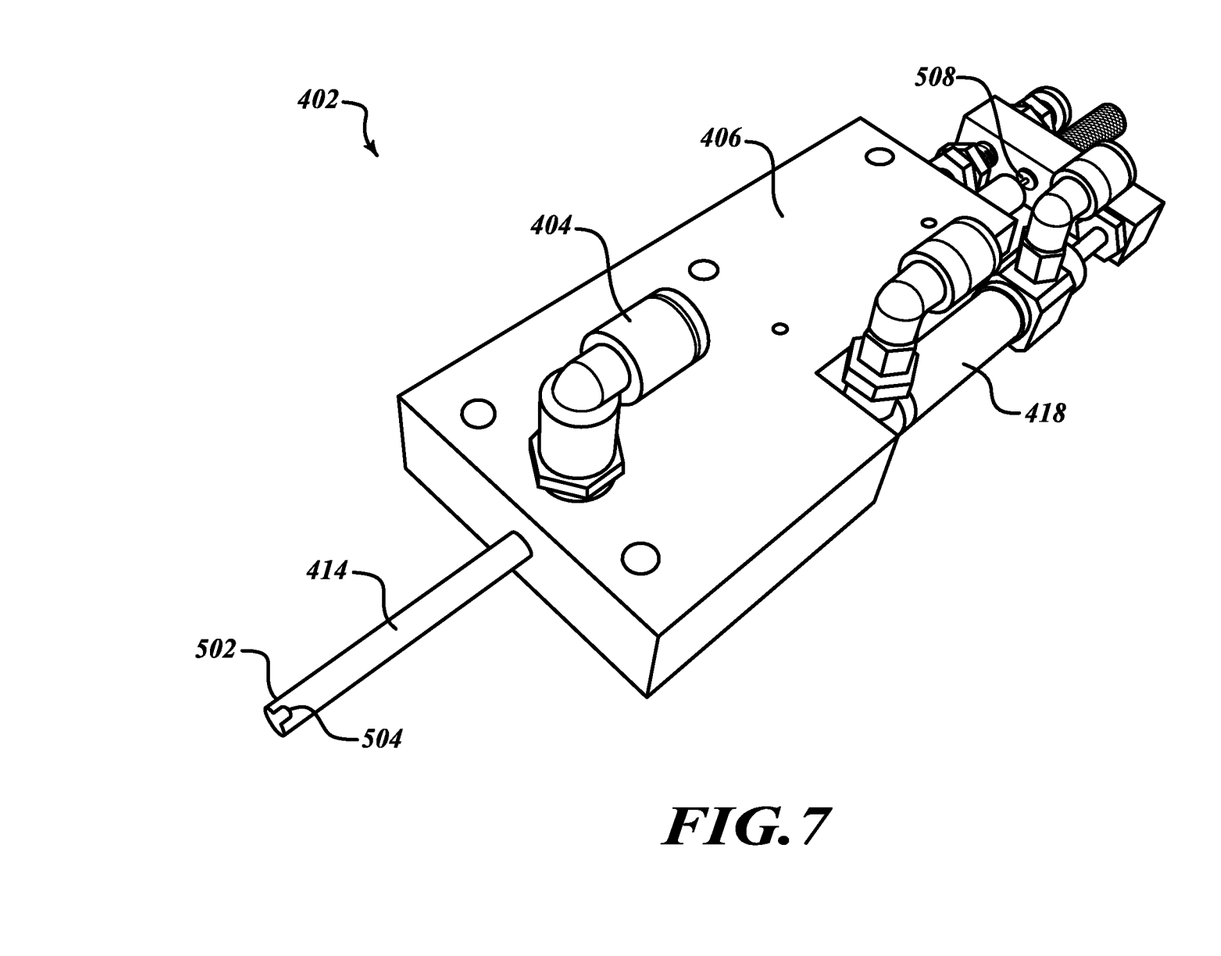
FIG. 7 is a schematic three-dimensional view of the insertion member and the release assistance rod in a retracted position according to embodiments of the disclosure.

Embodiments of the insertion device 402 further include an insertion member 414 and a release assistance rod 416, which are described in further detail with reference to FIGS. 6 and 7. In FIGS. 6 and 7, the insertion member 414 is shown arranged in the housing 406. In some embodiments, the insertion member 414 may have a substantially cylindrical or tubular shape. In some embodiments, other shapes that would be suitable to a person of ordinary skill in the art may be used. The insertion member 414 has an end 502. In some embodiments, the end 502 of the insertion member 414 may have a bell shape (e.g., outwardly extending sides). The end 502 of the insertion member 414 may also include a notched opening 504 as shown in FIGS. 6 and 7. In some embodiments, the insertion member 414 does not move with respect to the housing 406. The size of the insertion member 414 may be adjusted based on the size of the object being handled. Referring again to FIGS. 6 and 7, the release assistance rod 416 may be a solid rod made from metal, Teflon, or another suitable material arranged concentrically inside the insertion member 414. In some embodiments, the release assistance rod 416 may be hollow. The release assistance rod 416 has a proximal end 506 and a distal end 508 (not visible in FIGS. 6 and 7). If the insertion member 414 has a tubular shape, the release assistance rod 416 may also have a tubular shape. Accordingly, if the insertion member 414 has another shape, the release assistance rod 416 may be designed to fit inside the insertion member 414. The release assistance rod 416 is moveable within the insertion member 414 between an extended position (shown in FIG. 6) and a retracted position (shown in FIG. 7). In FIG. 6, the release assistance rod 416 is shown in the extended position with the proximal end 506 extending beyond the end 502 of the insertion member 414. In FIG. 6, the release assistance rod 416 is shown in the retracted position; therefore, the proximal end 506 is completely inside the insertion member 414 and is not visible.

Referring back to FIG. 4, the second vacuum pressure supply port 406 is shown connected to the insertion member 414. The second vacuum pressure supply port 406 is also connected to a vacuum pressure source (not shown). Accordingly, the second vacuum pressure supply port 406 may be configured to supply vacuum pressure to the proximal end 502 of the insertion member 414.

Figure 8:
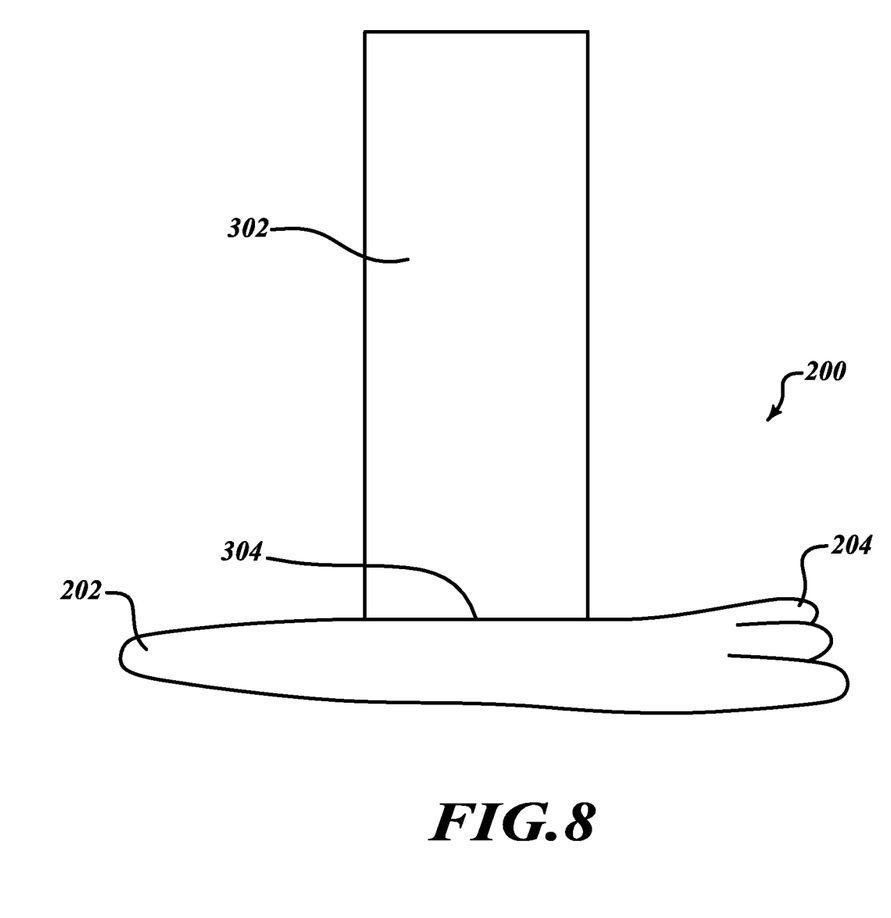
FIG. 8 is a side view of a pick-up device according to embodiments of the disclosure grasping the plant embryo.

Methods for using systems according to the disclosure for grasping and releasing objects will now be described with reference to FIG. 1 and FIGS. 8-12. In some embodiments, methods according to the disclosure include moving the pick-up device 114 to a first location to grasp the object (e.g., the plant embryo 200). In embodiments related to manufactured seed production lines, the pick-up device 114 may be moved over a single plant embryo 200 near the geometric center of the plant embryo 200 as shown in FIG. 8. A first vacuum pressure is supplied via the first vacuum pressure supply port 316 to the tip opening 304 of the pick-up device 114 enabling the pick-up device 114 to lift and hold the object.

Figure 9:
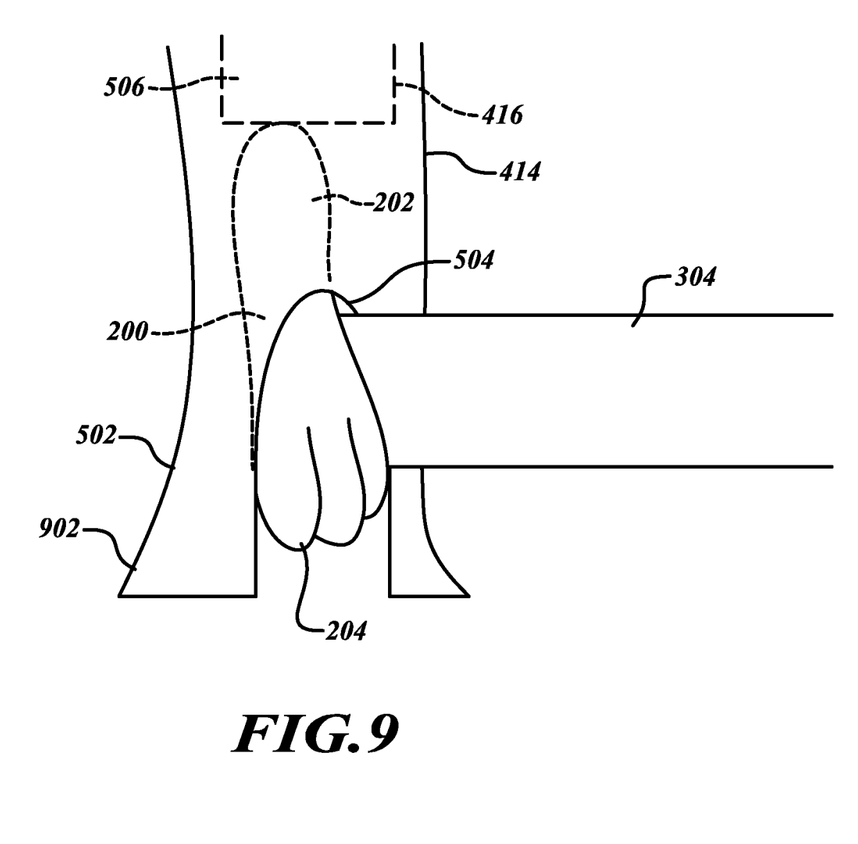
FIG. 9 is a side view of the plant embryo during handoff from the pick-up device to the insertion member according to embodiments of the disclosure.

The pick-up device 114 carrying the object (e.g., the plant embryo 200) is then rotated and translated (e.g., via the robotic arm 112) in order to move the object to a second location for transfer to the delivery assembly 104. As shown in FIG. 9, in some embodiments, the end 502 of the insertion member 414 has a bell shape 902. The notched opening 504 in the insertion member 414 allows the tip opening 304 of the pick-up device 114 to move close to the insertion member 414 and transfer the object. In some embodiments, this involves moving the pick-up device 114 in a direction that is substantially perpendicular to the insertion device 402, moving the insertion device 402 toward a receptacle opening 1002 (see FIGS. 10 and 11), and allowing the tip opening 304 of the pick-up device 114 to enter the notched opening 504 of the insertion member 414. In embodiments related to manufactured seed, the plant embryo 200 is transferred radicle (or root) end 202 first.

When the object is properly oriented, a second vacuum pressure is supplied (via the second vacuum pressure supply port 404) to the insertion member 414 so that it may grasp the object. In some embodiments, the release assistance rod 416 is in the retracted position during this process to limit insertion distance of the object. When the object has been successfully transferred, the first vacuum pressure is removed and the pick-up device 114 may be retracted away from the delivery assembly 104. In some embodiments, a puff of compressed air may be released through the pick-up device 114 to facilitate transfer of the object to the insertion member 414. Additionally, in some embodiments, one or more puffs of compressed air may be used to clean the pick-up device 114 and prepare it for grasping another object. In some embodiments (e.g., FIG. 10) the pick-up and delivery system 100 includes an air filter 1002 to sterilize the air around the object.

Figure 10:
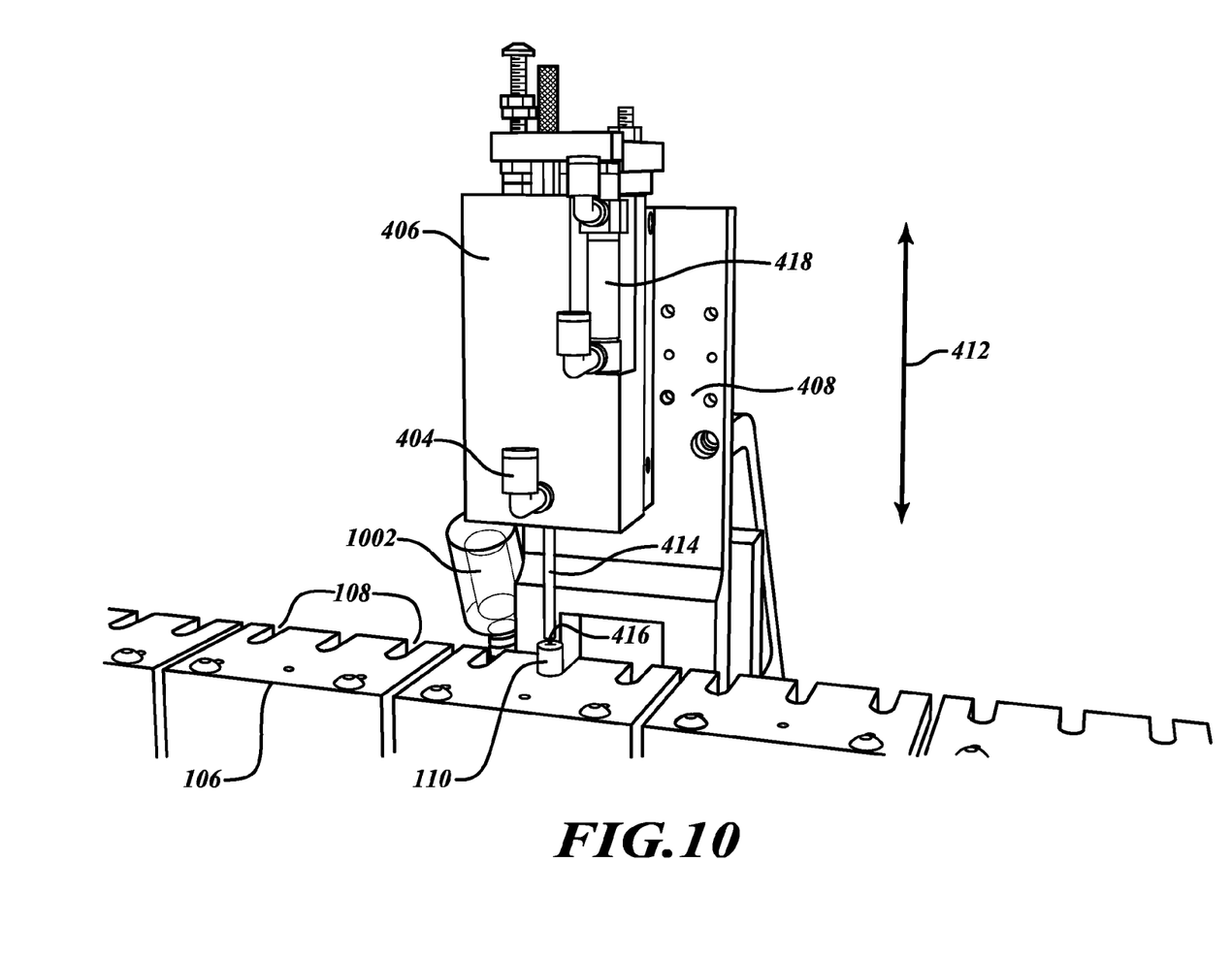
FIG. 10 is a schematic three-dimensional view of the delivery assembly in a second position during embryo insertion.
Figure 11:
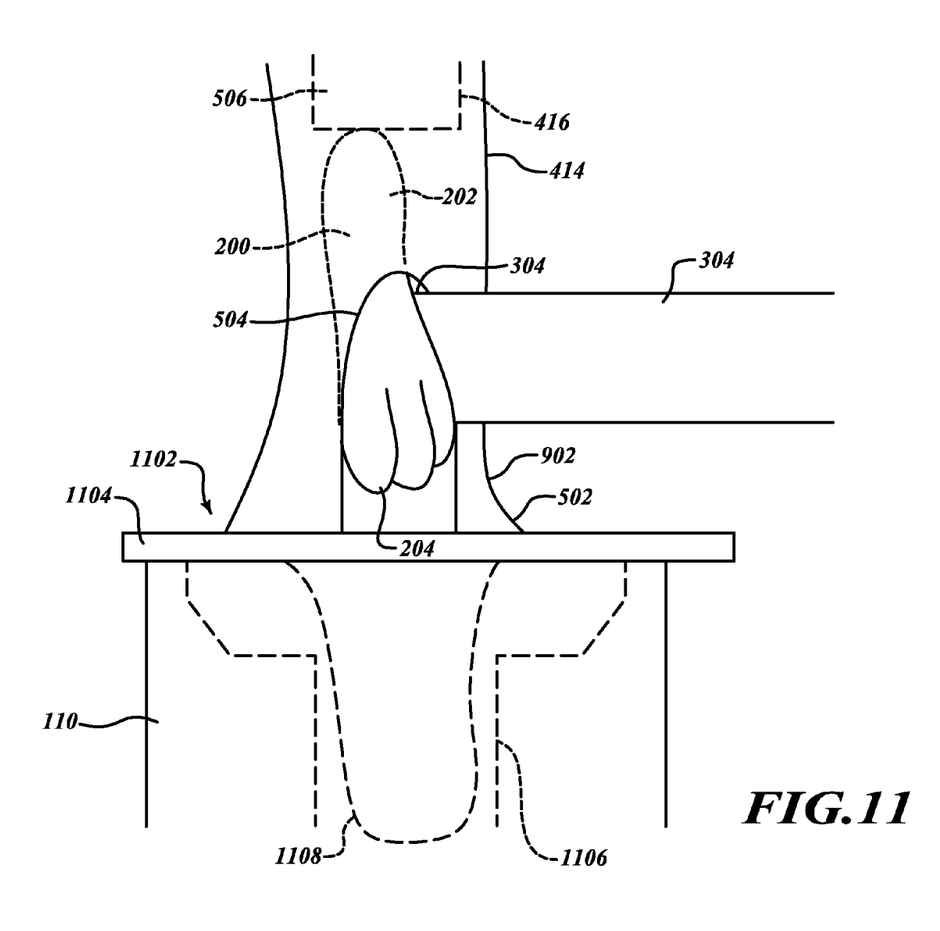
FIG. 11 is a side view of the plant embryo during insertion into a receptacle.

After the object has been successfully transferred from the pick-up device 114 to the insertion member 414, the insertion device 402 and the object may be moved to the second position as shown in FIG. 10 if not already in that position. In embodiments related to manufactured seed, the receptacle 110 is a seed blank having a receptacle opening 1102, a washer 1104, and a cotyledon restraint 1106 (see FIG. 11). The object may be partially inserted into the receptacle 110 or may be held directly above the receptacle opening 1102 as shown in FIG. 11.

Figure 12:
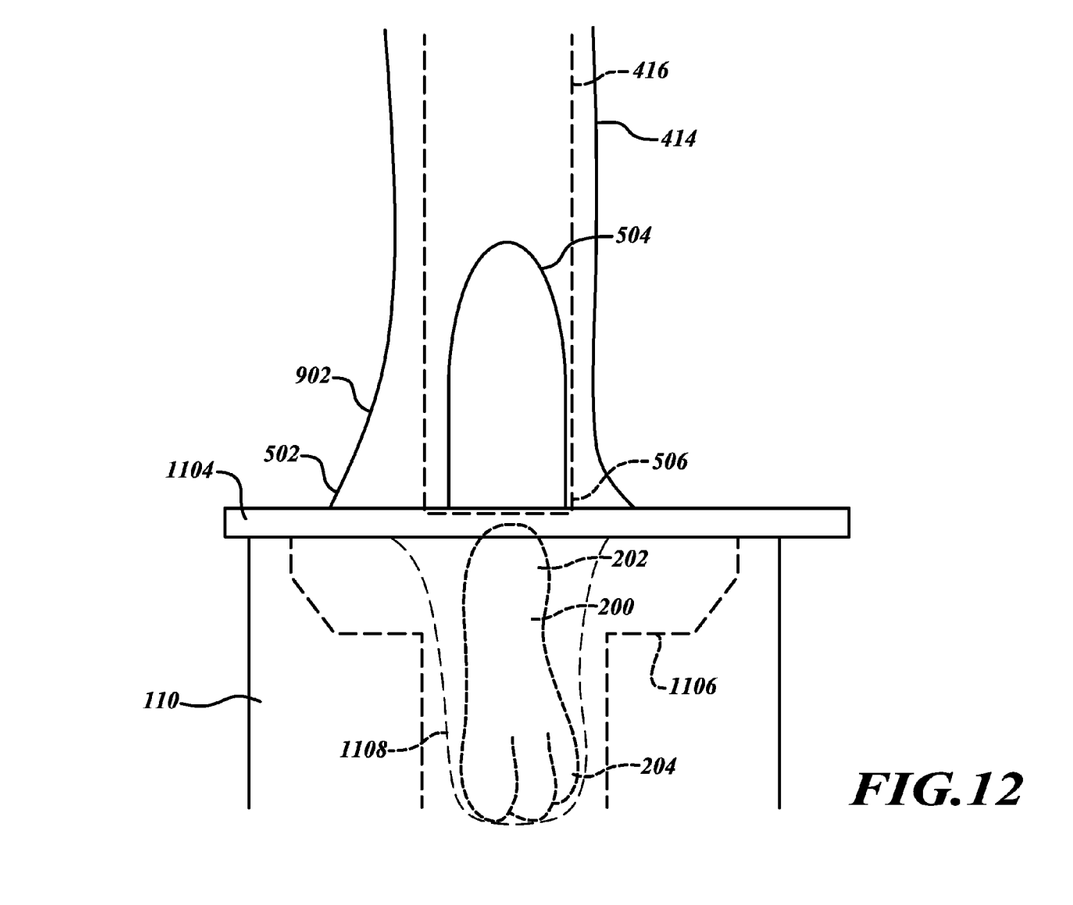
FIG. 12 is a side view of the plant embryo after insertion into the receptacle.

The object may then be inserted into the receptacle 110 by removing the second vacuum pressure and moving the release assistance rod 416 to the extended position as shown in FIG. 12. In some embodiments, insertion of the object into the receptacle 110 may be facilitated by releasing a puff of compressed air through the insertion member 414. In embodiments related to manufactured seed, after the plant embryo 200 has been deposited into the receptacle 110, the receptacle may be sealed according to methods well known to person of ordinary skill in the art.

From the foregoing, it will be appreciated that the specific embodiments of the disclosure have been described herein for purposes of illustration, but that various modifications may be made without deviating from the disclosure. For example, minor modifications to the mechanical components of the pick-up assembly 102 and delivery assembly 104 that would be obvious to a person of ordinary skill in the art are within the scope of the disclosure. Further, the shapes and operation of specific components may be modified in a manner that would be obvious to a person of ordinary skill in the art without departing from the spirit of the disclosure.

Aspects of the disclosure described in the context of particular embodiments may be combined or eliminated in other embodiments. For example, aspects of the disclosure described with respect to manufactured seed applications may be used in applications related to other material handling systems. Further, while advantages associated with certain embodiments of the disclosure may have been described in the context of those embodiments, other embodiments may also exhibit such advantages, and not all embodiments need necessarily exhibit such advantages to fall within the scope of the disclosure. Accordingly, the invention is not limited except as by the appended claims.

The invention claimed is:

1. A pick-up and delivery system comprising:
a pick-up assembly comprising:
    a robotic arm;
    a pick-up device rotatably mounted on the robotic arm; and
    a first vacuum pressure supply port operably connected to the pick-up device; and
a delivery assembly comprising:
    an insertion device separate from the pick-up device, the insertion device moveable between a first position and a second position, the insertion device comprising:
        an insertion member having an end; and
        a release assistance rod arranged inside the insertion member, the release assistance rod being moveable between an extended position and a retracted position;
    a second vacuum pressure supply port operably connected to the insertion member; and
    wherein the release assistance rod has a proximal end and a distal end; and
    wherein the proximal end of the release assistance rod extends beyond the end of the insertion member when the release assistance rod is in the extended position.

2. The pick-up and delivery system of claim 1 wherein the proximal end of the release assistance rod is completely inside the insertion member when the release assistance rod is in the retracted position.

3. The pick-up and delivery system of claim 1 wherein the insertion member has a substantially cylindrical shape.

4. The pick-up and delivery system of claim 1 wherein the end of the insertion member has a notched opening.

5. The pick-up and delivery system of claim 1 wherein the end of the insertion member has a bell shape.

6. The pick-up and delivery system of claim 1 wherein the pick-up device comprises a first section having a first diameter, a second section having a second diameter, and a tip opening.

7. The pick-up and delivery system of claim 6 wherein the first vacuum pressure supply port is configured to supply a first vacuum pressure to the tip opening of pick-up device.

8. The pick-up and delivery system of claim 1 wherein the second vacuum pressure supply port is configured to supply a second vacuum pressure to the proximal end of the insertion member.

9. A pick-up and delivery system comprising:
a storage assembly comprising one or more cavities, each of the one or more cavities being configured to hold a receptacle, each receptacle being configured to hold an object, the object being about 0.2 to about 10.0 millimeters wide and about 2.0 to about 20 millimeters long;
a pick-up device rotatably mounted on a robotic arm;
a first vacuum pressure supply port operably connected to the pick-up device;
a frame arranged in a plane substantially perpendicular to the storage assembly;
a housing mounted on the frame, the housing being moveable on the frame between a first position and a second position in a plane substantially perpendicular to the storage assembly;
an insertion device separate from the pick-up device, the insertion device comprising:
    a tubular insertion member having an end having a notched opening; and
    a release assistance rod arranged inside the tubular insertion member, the release rod being moveable between an extended position and a retracted position; and
a second vacuum pressure supply port operably connected to the tubular insertion member;
wherein the release assistance rod has a proximal end and a distal end; and
wherein the proximal end of the release assistance rod extends beyond the end of the tubular insertion member when the release assistance rod is in the extended position.

10. The pick-up and delivery system of claim 9, further comprising an actuation assembly for the release assistance rod, the actuation assembly comprising at least one of hydraulics and electronics.

11. The pick-up and delivery system of claim 9 wherein the pick-up device comprises one or more cylindrical tubes and a tip opening, the tip opening having an outer diameter ranging from about 0.04 inches to about 0.08 inches and an inner diameter ranging from about 0.02 inches to about 0.06 inches.

12. The pick-up and delivery system of claim 11 wherein portions of the one or more cylindrical tubes are covered in a substance effective to reduce reflectivity of the pick-up device.

13. The pick-up and delivery system of claim 9 wherein the object is a plant embryo.

14. The pick-up and delivery system of claim 9 wherein the receptacle is a cotyledon restraint.

\* \* \* \* \*